United States Patent

Petersen et al.

[11] 4,212,996
[45] Jul. 15, 1980

[54] PROCESS FOR THE SIDE-CHAIN CHLORINATION OF PERHALOGENATED METHYL AROMATIC COMPOUNDS

[75] Inventors: Egon N. Petersen, Neunkirchen-Seelscheid; Hermann Richtzenhain, Much-Schwellenbach; Klaus Schrage, Königswinter-Uthweiler, all of Fed. Rep. of Germany

[73] Assignee: Dynamit Nobel AG, Troisdorf, Fed. Rep. of Germany

[21] Appl. No.: 905,662

[22] Filed: May 15, 1978

Related U.S. Application Data

[63] Continuation of Ser. No. 709,057, Jul. 27, 1976.

[30] Foreign Application Priority Data

Jul. 31, 1975 [DE] Fed. Rep. of Germany ....... 2534210

[51] Int. Cl.$^2$ .................... C07C 41/00; C07C 17/14
[52] U.S. Cl. ................. 568/639; 260/651 R; 560/221
[58] Field of Search .............. 260/612 R, 651 R; 568/639

[56] References Cited

U.S. PATENT DOCUMENTS

| | | | |
|---|---|---|---|
| 2,994,653 | 8/1961 | Miller | 260/651 R X |
| 2,998,459 | 8/1961 | Baker et al. | 260/651 R X |
| 3,004,072 | 10/1961 | Doedens et al. | 568/639 |
| 3,170,959 | 2/1965 | Trapp | 260/612 R X |
| 3,275,708 | 9/1966 | Bylsma | 260/612 R X |
| 3,419,626 | 12/1968 | Pyne et al. | 260/651 R |
| 3,883,481 | 5/1975 | Kopetz et al. | 568/641 X |
| 3,928,478 | 12/1975 | Johnson | 260/651 R |
| 3,965,197 | 6/1976 | Stepniczko | 260/612 R X |

FOREIGN PATENT DOCUMENTS 1550774 11/1968 France ................. 260/651 R
1364397 8/1974 United Kingdom .

*Primary Examiner*—Bernard Helfin
*Attorney, Agent, or Firm*—Sprung, Felfe, Horn, Lynch & Kramer

[57] ABSTRACT

Process for the side-chain chlorination of aromatic compounds completely halogenated in the nucleus, containing methyl groups, and having the general formulas:

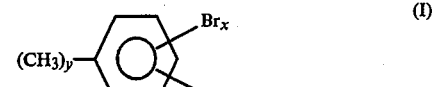

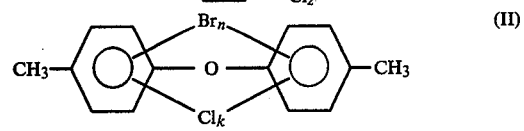

wherein y=1 or 2, z=0 to 1, x=6−(y+z), n=0 to 8 and k=(8−n) and the methyl groups are, respectively, in the ortho, meta or para position to one another and in the p-position to the oxygen bridge, by thermal chlorination in the liquid phase. The bis-monochloromethyl compounds of formula (II) are novel compounds. The chlorination products are useful as intermediates.

21 Claims, No Drawings

PROCESS FOR THE SIDE-CHAIN CHLORINATION OF PERHALOGENATED METHYL AROMATIC COMPOUNDS

This is a continuation, of application Ser. No. 709,057, filed July 27, 1976.

BACKGROUND

The subject matter of the present invention is a process for the side-chain chlorination of aromatic compounds which are completely halogenated in the nucleus and contain methyl groups, and have the following general formulas:

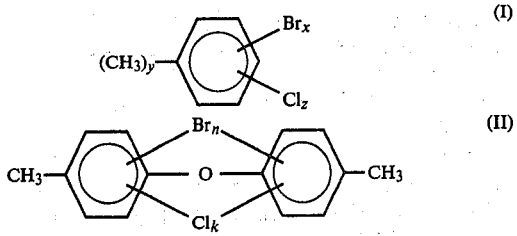

wherein $y=1$ or 2, $z=0$ to 1, $x=6-(y+z)$, $n=0$ to 8 and $k=(8-n)$, and the methyl groups are in the ortho, meta or para position to one another and in the para position to the oxygen bridge, respectively.

Also subject matter of the invention are 4,4'-bis(-chloromethyl)-ar-octahalogendiphenylethers and 4,4'-bis(halogenmethyl)-ar-octahalogendiphenylethers wherein 0.01 to 0.5 Br and 1.5 to 1.99 Cl are divided between the two halogen methyl groups. The compounds are highly brominated in the nucleus and mixtures beginning from $Br_6Cl_2$ and extending up to $Br_8$, and especially those beginning from $Br_7Cl_1$, are of especial value.

It is known that methyl aromatics containing chlorine in the nucleus can be successfully chlorinated on the side chain to form technically useful chloromethyl derivatives, but usable processes for the side-chain chlorination of corresponding compounds which are perbrominated in the nucleus are lacking.

If the attempt is made to apply the side-chain chlorination methods commonly used with compounds chlorinated in the nucleus to the analogous methyl aromatics perbrominated in the nucleus, either these methods frequently fail entirely, or, if more severe conditions are applied, a considerable exchange of chlorine for the bromine bound to the nucleus takes place.

Another considerable difficulty arises from the fact that aromatics brominated in the nucleus are prepared as a rule with the use of iron or iron compounds or other metal compounds as catalysts like aluminium chloride. In the large-scale production of these bromine compounds, small amounts of iron always remain in the bromination product, and they can be removed only at considerable expense. But even traces of iron accelerate the exchange of chlorine for bromine in the side-chain chlorination of brominated methyl aromatics, and do so to such an extent that very inconsistent reaction mixtures are obtained which are of scarcely any economical use.

THE INVENTION

A procedure has now been found which makes it possible in a simple, economical manner to prepare chloromethyl aromatic compounds brominated in the nucleus from the substances of General Formula I and/or II.

The following methyl aromatic compounds perhalogenated in the nucleus can be used, for example, as starting substances with good success: pentabromotoluene, tetrabromo-o-xylene, tetrabromo-m-xylene, tetrabromo-p-xylene, mixtures thereof, octabromoditolylether, octachloroditolylether, as well as octa(bromo, chloro)-ditolylether and perhalogenated xylenes and toluene containing mainly bromine and up to one chlorine as substituents in the aromatic nucleus, which can be prepared advantageously by bromochlorination with BrCl, and other such compounds.

The chloromethyl-perhalogen-aromatics which can be obtained from these by the method of the present invention are produced with good uniformity and in high yields. They constitute valuable intermediates which can be further processed to tetrabromoxylyleneglycols, pentabromobenzylacrylate, tetrabromoxylylenediacrylates, or the oligomeric and polymeric formals of the glycols—as a rule without further purification of the chloromethyl compounds.

Sequential reactions of this kind are described, for example, in U.S. Ser. No. 589,958, filed June 24, 1975 (Group 127) and Ser. No. 681,672, filed Apr. 29, 1976

The process of the present invention consists in the thermal chlorination of the starting substances of General Formulas I and II in an inert diluent or solvent or suspending agent, in the presence of a complex forming agent for metals, the complex forming agent being selected such that its activity is assured even at the higher temperatures used for the chlorination.

Chlorination in substance, i.e., in the melted, undiluted starting materials, is also successfully practicable, especially if the melting point of the starting material and of the chloromethyl compound that is formed is not substantially higher than 200° C.

The procedure of the invention is to suspend the substance to be chlorinated in the inert diluent, add the complex former, then heat the mixture to the reaction temperature, and, after this temperature is reached, to begin feeding in the chlorine.

The chlorination are advantageously performed in a temperature range between 150° and 230° C., and to special advantage they are performed at 170° to 200° C. The pressure is preferably the self-pressure of the reactants, although a slight over-pressure is possible.

The chlorine is fed in at such a rate that the amount of chlorine presented for reaction is not greater or only slightly greater than the amount that will react to chlorinate the side chain. A greater amount than will be used up immediately by the reaction is to be avoided, since excess chlorine leads to an exchange with bromine in the nucleus, thereby impairing the outcome of the process. An excessive rate of input of the chlorine will manifest itself visibly by the formation fo bromine vapors in the reaction vessel.

Surprisingly, there is no need to fear any overchlorination of the side chains to $-CHCl_2$ much less $-CCl_3$, since once the formation of the $CH_2Cl$ groupings is completed, the input of additional chlorine results in halogen exchange in the nucleus, which is immediately manifested by the formation of bromine.

The fact that, during the substitution, the chlorination proceeds virtually exclusively in favor of the benzyl chloride stage represents a great advantage of the process of the invention, for in most conventional side-chain chlorinations, mixtures of benzyl chlorides and benzal chlorides are obtained, usually along with an amount of the corresponding benzotrichlorides.

Also, since the chloromethyl compounds produced are crystallized out to a great extent by the cooling of the reaction mixtures, it is easy and economical to isolate them by suction filtration or centrifugation.

Liquids which are inert under the conditions of the chlorination are to be used as diluents, those having boiling points above 190° C. being used to special advantage. The use of hexachlorobutadiene as the reaction medium has proven to be especially advantageous in the performance of the process of the present invention, although other chlorides of aliphatic hydrocarbons atoms can also be used, with boiling points above 190° C.

Furthermore, the diluent does not need to be replaced for each batch, but can be used repeatedly, without previous refinement by distillation, and this is a distinct economic advantage.

The weight ratio of the starting compound to the diluent is advantageously from 1:1 to 1:6.

Suitable masking agents for metal traces, especially iron traces in the starting material, and only those substances which are sufficiently stable at 180° C. to 230° C., at reaction temperature and are still effective at these temperatures under the conditions of the reaction.

The following, for example, have proven to be suitable complexing compounds: cyclohexylene-(1,2)-dinitrilotetraacetic acid, bis-(aminoethyl)-glycolether-N,N,N',N'-tetraacetic acid, [3-aza-3-(carboxymethyl)]-pentamethylene-dinitrilotetraacetic acid; however, ethylenediaminetetraacetic acid is used to very special advantage. Of these compounds from 0.01 to 1% is used in the performance of the process of the invention, with respect to the bromine compound, depending on the iron content of the starting material.

In general such complexing compounds have 3 to 5 reacting groups one may be N in form of e.g. amino groups and the other carboxylic groups. One more of these may be nitrolo triacetic acid.

By the reaction of the invention the methyl group is converted into the monochloro methyl group. The m-, p- and o-isomers of tetrabromoxylylene dichlorides and the tetra (bromo, chloro) compounds can been converted into the tetrabromoxylylene diacrylates or dimethacrylates and tetra (bromo, chloro) di(meth)acrylates while pentabromobenzyl chlorid and penta(bromo, chloro) benzyl chlorid results pentabrombenz acrylates or methacrylates, the products and the process of preparing beeing more closely described in application Ser. No. 589 958 (group 126).

In general these (meth) acrylates and di (meth) acrylates can be produced by contacting an alkalisalt e.g. an sodium or potass um slat of methacrylic or preferably acrylic acid in polar solvents (which are miscible to at least some degree with water) with chloromethyl compounds as named above favorably at 50° to 150° C., preferably 80° to 150° C., and usually in the presence of a polymerization inhibitor, whereby the chlorine of the chlorometh group is converted into the (meth) acrylic ester group. Favourably no aromatic bound halogene does react. The said solvent may be preferably ethyleneglycol monomethylethe or solvents like alcohols of $C_1$ to $C_4$, glycols up to 6 carbon atoms, dimethylformamide, dimethylsulfoxide, etc. The alkali (meth) acrylats may been produced from an alkali sour e.g. alkali hydroxide in 50% aqueous solution or alkalicarbona in stoichiometric excess of 1 to 10 mol-% and the (meth) acrylic acid at 10° to 80° C., preferably in said solvents. The reaction may be performed by equivalent amount of alkali(meth) acrylate and monochloromethyl compound in good yields and purity during 0,5 to 5 hours. Suitable inhibitors are hydrochinone, p-benzochinon or hydrochinone monomethyl ether. For example Tetrachloro-m-xylylene diacrylate is produced from 11,3 g of sodium carbonate under stirring and current of $N_2$ by addition of 15,2 g of acrylic acid (0,28 mole) plus 14 g hydroquinone in 180 ml of methylglykole at 60° C. To the solution of the salt 49.1 g of tetrachloro-m-xylylene chloride was added and heated for 2,5 hours at 110° C.

The solution was hot filtered and then cooled in an ice bade. The crystallizate was filtered, washed free of NaCl and dried.

Crude yield 42.5 g (75,5% of the theory)
Purity 98.5%
Melting point: 105°–108° C.

In analogous manner tetrabromo-o-xylylene diacrylate of M.P. 92°–99° C. and tetrabromo-p-xylylene diacrylate of M.P. 125°–128° The so produced unsaturated esters of the formula

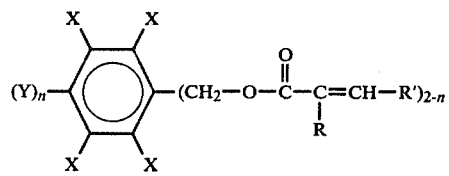

in which X represents bromine or chloride, Y methyl or bromine, n=0 or 1, and R and R' each represents hydrogen or a methyl group may used as flame retarding agents in the way and amounts as described below for the polymers produced there from.

The unsaturated esters of Formula III furthermore are very useful for the production of polymers and copolymers containing the structural unit

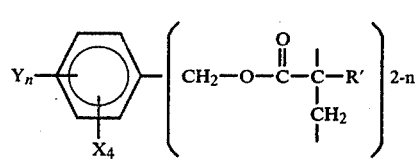

wherein, Y X, R' and n have the same meaning than in Formula II

As to diesters, in which is n=0, the p-compounds or mixtures o m- and o-acrylates are preferred. As to monoesters the pentabrom compounds and the pentahalogeno compounds with three and more substituted bromine and two or less substituted chlorine in the aromatic ring are preferred.

These polymers may be produced by means of polymerization proces in solution of organic solvents as benzene or in aqueous suspension or dispersion as well as in substance i.e. essentially without presence of solvents or diluents.

Radical polymerization catalysts as azo compounds like azois butyronitrile or peroxides like dibenzoyl or dicumyl peroxide or peroxidisulfate are useful at temperatures of 0 to 150 centigrade celsius.

Where copolymers are produced preferred comonomers are ethylenical unsaturated as styrene, acrylonitrile, acrylic or methacrylic acid esters of 1 to 6 C-atoms in the alcohol group, unsubstituted xylylene acrylates and methacrylates as well as chloro substituted monomers as discribed herein, furthermore butadiene, isoprene, fumaric or maleinic acids, the polyesters thereof and the anhydride of the latter and other like vinyl chloride and vinylidene chloride.

More than one comonomer may be present, such forming modified terpolymers like bromine containing ABS ore MBS from the acrylates, in case of further acrylic acid esters, acrylonitrile, methacrylic acid esters in presence of styrene on a polymer base of polybutadiene or polyisoprene. Polymers and copolymers so formed are thermoplastic in case of one present acrylic or methacrylic ester group when in formula IV is n=1 and are crosslinked and not meltable in presence of two ester groups when in formula IV is n=0.

In case of homopolymers and in case of copolymers with high contents of monomer of formula III in the range of 40 to 99,9 wt-% of prepared copolymers bromine contents of 35 to 85, preferred 45 to 75 wt-%, sometimes additionally chlorine being present, are produced, which are very valuable flame retarding additives to polyesters, polyurethanes, polyacetales, ABS and MBS and other polymers.

In case of copolymers of lower contents of 2, preferred 5 to 40 wt% monomers of formula III they it-self are valuable flame retardant polymers, especially in cases of bromine contents of 1 to about six or eights wt%.

Both groups of polymers and copolymers are not able to sweep out of polymer products as to high melting points of at least 150° C. or their inmeltibility and therefor giving the most valuable attribute to polymer products to have are durable flame retardence for a very long time even at high temperature of surrounding.

Furthermore surprisingly polymers and copolymers are unsoluble in all common solvents, so attributing to polymer products a prevention from attack of liquid or gaseous solvents during th use.

Examples for such polymers are polypentabromobenzylacrylate or polytetrabromo mono chloro benzylacrylate and corresponding methacrylates, being polymerizable at e.g. 60°-120° C. in methylglycol in presence of e.g. benzoylperoxide (2-6 g pe 200 g monomer) in a yield of 95 to 99 wt.%, containing about 68 to 73 wt.% bromine, being meltable at 200° to 220° C. having a low weight loss of 2% at 206° C. during 72 hours. These polymers in amounts of e.g. 10 wt.% can be incorporated in polymers e.g. together with 5 wt.% $Sb_2O_3$ and 30 wt.% glass fiber in 55 wt.% poly-butylen-terephthate or poly-ethylen-tere phthalate.

Products formed therefrom beeing superior flame retardent acco ding test of Underwriters Laboratory UL 94, even after worm storage for 7 days at 70° C. still having the best value of VO. No sweping out was observed after 7 days storage at 150° C. Other examples for such polymers are polytetrabromoxylylenebisacrylate and -bismethacrylate, both beeing unmeltable, and poly-tetrabromoxylylacrylate which are polymerised in quite similar way and beeing used as flame retardents of the same good behavior.

Products of Formula III itself may be added as flame retardents in common plastic products of polymers as mentioned above, pol ethylen etc.

These polymers and the process for production is more closely referred to in our application.

The bis(chloromethyl) octahalogenodiphenylether produced from compounds of formula II in quite corresponding manner can form bis (meth) acrylates by reaction of each of the chloromethyl-group mit alkali (meth-)acrylates under conditions noted above for the brominated xylylene (meth) acrylates.

The named ether bisarylates may used itself as flame retardents in amount and manner as noted for the tetrabromo xylenyl bisacrylates or may be polymerized or copolymerized and then form flame retardent additives or flame retardent polymer products as noted for the polymers containing incorporated the structural unit (IV).

The process für the production of this polymers also is quite similar to the above noted polymerization process of products containing unit of formula IV, bearing in mind that two moles (meth) acrylate salt form the equivalent of one mole of the bis (chlormethyl) compound.

The polymers and copolymers are reticuled according the two unsaturated acid groups in the monomer and are of very considerable stability against high temperature up to 280° C. or more, which fact results good stability during working of the polymers or plastics containing this polymers and a very low rate of sweeping out or diffusion of the flame retardent out of the plastic product, protected against inflamation and burning.

While the polymers and copolymers are valuable flame retardent additives it is a preferred embodiment to form copolymers beeing itself flame retardent plastic products.

This by copolymerization with usual ethylenical unsaturated monomers as above all (meth) acrylic esters, acrylonitrile, styre ethylene etc. is effected to form above all styrolic bisacrylate resins or unsaturated polyester resins or sulutions of these, the latter formed of ethylenglycol or neopentylglycol or both, fumaric acid and phthalic or terephthalic acid or their methyl esters with contents of 5-20% of said brominated (meth) acrylates as well as of ditolylether or of the xyloles, as more closely discribed in german application P 26 12 843, 8, filed May 26, 1976.

EXAMPLES

The following examples are intended to explain the invention and the methods of the invention, without, however, limiting them.

Unless otherwise stated, the percentages given are percentages by weight.

EXAMPLE 1—Preparation of pentabromobenzylchloride

In a four-necked flask equipped with stirrer, thermometer, condenser and gas introduction tube, 486.7 grams (1 mole) of pentabromotoluene having a melting point of 284°-287° C. and an iron content of 68 ppm are suspended in 700 ml of hexachlorobutadiene; to mask the traces of iron, 490 mg (0.1 wt.-% with respect to the pentabromotoluene) of ethylenediaminetetraacetic acid is added, and this mixture is heated at 175° to 180° C.

At this temperature, chlorine is introduced into the liquid or onto the surface of the slowly stirred suspension at such a rate that little or no chlorine appears in the exhaust gas in addition to the hydrogen chloride that is formed.

The required amount of chlorine can be conveniently introduced over a period of about 120 to 150 minutes, the absorption proceeding slowly toward the end of the reaction.

The starting material passes completely into solution during the chlorination, and the end of the reaction at the benzyl chloride stage can be identified by the fact that bromine vapors appear even if a small amount of chlorine is put in.

Then the chlorine feed is shut off and the reaction mixture is allowed to cool. The chlorination product separates largely by crystallization. It is suction filtered, washed with petroleum ether, and dried.

453 g (87%) of a yellow-brownish crystallizate is obtained, having a melting point of 162°–166° C. This, when recrystalized from cyclohexane at 1:20, yields pale yellow acicular crystals with a melting point of 170°–172° C., whose analysis corresponds substantially to that of pentabromobenzyl chloride. $C_7H_2Br_5CL$ (521.10)

Calculated: C 16.13%, H 0.39%, Br 76.68%, Cl 6.80%; Found: C 16.44%, H 0.40%, Br 76.80%, Cl 6.30%.

The NMR spectrum indicates that the substance is not entirely homogeneous, a Cl/Br exchange having taken place in the nucleus, and the exchanged bromine having attached itself to the side chain.

From the elemental analysis of the pentabromobenzyl allyl ether prepared from the chlorination product and having a melting point of 101°–103° C., it appears that the chlorine content in the nucleus is approximately 2.5% by weight.

For comparison, we prepared pure pentabromobenzyl bromide from pentabromotoluene and bromine in hexachlorobutadiene at 175°–185° C. The side-chain bromination is difficult also at these temperatures, and is successful only in the presence of radical formers. We used azodiisobutyronitrile and obtained the pentabromobenzylbromide in a 92% crude yield (melting point 175°–179° C.). When it was recrystallized from cyclohexane in a ratio of 1:20, the melting point was 185°–187° C. The allyl ether prepared therefrom melts pure at 106°–107.5° C., i.e., only a few degrees higher than the pentabromobenzylallyl ether prepared from the chlorination product of pentabromotoluene.

EXAMPLE 2—Preparation of tetrabromoxylylenedichloride (a) Single Experiment

In the apparatus described in Example 1, 2.1 liters of technical hexachlorobutadiene and 1.688 kg (4 moles) of tetrabromoxylene (isomer mixture of 21.1% o-, 50% m- and 28.9% p-), melting point 249°–250° C., and having an iron content of 15 ppm, plus 1.75 g of ethylenediaminetetraacetic acid, were heated with stirring on an oil bath at 170° to 180° C. When this temperature is reached in the reaction mixture, the introduction of chlorine is begun, as described in Example 1. During the main reaction period the bath temperature is maintained at about 175° C., since the internal temperature increases to about 188°–190° C. due to the heat of reaction. After a weight increase of 267 g (theory 276 g) had been reached in about 5 to 6 hours, bromine vapors became clearly visible. The introduction of chlorine was stopped.

The processing of the mixture was performed as described in Example 1, since this compound, too, largely crystallizes out of the chlorination mixture when it cools, in pale yellow to brownish crystals.

1.507 kg of raw product (77%) melting at 161°–174° C. was obtained.

When the raw product was recrystallized from acetic ester in a ratio of 1:16, pale yellow crystals were obtained, which melted at 167°–173° C. and gave the following analysis: $C_8H_4Br_4Cl_2$ (490.67).

Calculated: C 19.58%, H 0.82%, Br 65.15%, CL 14.45%; Found: C 19.56%, H 0.65%, Br 67.10%, Cl 12.70%.

The substance can also be recrystallized from methoxyethylchloride at 1:6.

By cooling the hexachlorobutadiene mother liquor, an additional 108 g of crystallizate was obtained (5.5%), melting point 151°–175° C. By concentrating the mother liquor in vacuo, virtually quantitative yields are obtained. The substance which can still be obtained in this manner is brown in color and melts at about 103°–108° C. Upon recrystallizing it from benzine at 1:4 (with the addition of charcoal) we obtained virtually colorless needles of a melting point of 101°–104° C., having the following analysis:

C 20.55%, H 0.88%, Br 63.80%, Cl 15.00%.

(b) Series experiments using the mother liquor of each preceding experiment.

In each of these experiments, 1.265 kg (=3 moles) of tetrabromoxylene of the same composition as in the experiment before it was chlorinated at 175° to 180° C. in 2.1 liters of solvent. Each time fresh hexachlorobutadiene was added to the mother liquor to make 2.1 liters for reuse. The color of the raw product did not change substantially in the course of the series of experiments, so that even the product of Batch 5 was still quite light.

The outcome of the series of experiments is summarized in the following table.

Table 1

| Batch No. | Chlorine introduction time in minutes | Yield Kg | % | Melting Point °C. |
|---|---|---|---|---|
| 1 | 360 | 0.963 | 65.6 | 160–175 |
| 2 | 360 | 1.182 | 80.4 | 145–175 |
| 3 | 340 | 1.212 | 82.4 | 144–172 |
| 4 | 340 | 1.270 | 86.4 | 132–170 |
| 5 | 350 | 1.306 | 88.9 | 129–168 |
| | Average yield | | 80.6 | |

113 g of not very pure product (6) of a melting point of 93°–99° C. was obtained by freezing it out at −20° C. from the mother liquor of Batch 5.

As Table 1 shows, the yield clearly improves from Batch 1 to Batch 5. On the other hand, the melting points diminish, which evidently indicates an increasing lack of homogeneity in the chlorination products. To gain a better understanding, the chlorine and bromine content of all of the products was determined. Furthermore, the products were each transformed to their corresponding glycol to enable the content of chlorine and bromine in the nucleus alone to be determined. Also, the melting points of the glycols were determined.

The following Table II gives the results of these studies.

Table II

| Batch No. | Dichloride: M.P. °C. | % Br | % Cl | Glycol: % Br | % Cl | Yield | M.P. °C. |
|---|---|---|---|---|---|---|---|
| 1 | 160–175 | 66.2 | 13.3 | 67.1 | 2.8 | 80% | 249–252 |
| 2 | 145–175 | 66.5 | 13.4 | 66.9 | 3.2 | 79% | 247–251 |
| 3 | 144–172 | 66.4 | 13.7 | 67.5 | 3.0 | 81.7% | 248–252 |
| 4 | 132–170 | 66.8 | 13.5 | 67.1 | 2.7 | 80.9% | 247–251 |
| 5 | 129–168 | 66.5 | 13.4 | 67.2 | 2.7 | 79.9% | 247–251 |
| 6 | 93–99 | 61.9 | 17.4 | 65.9 | 3.8 | 75.2% | 242–246 |

6 = Substance from the mother liquor of Batch 5.
Calculated for pure dichloride: $C_8H_4Br_4Cl_2$ (M. Wt 490.67) C 19.58%, H 0.82%, Br 65.15%, Cl 14.45%
Calculated for pure glycol: $C_8H_6Br_4O_2$ (M.Wt. 453.78) C 21.18%, H 1.33%, Br 70.44%, O 7.05%.

This tabulation and comparison clearly shows that in the case of chlorination batches 1 to 5 scarcely any differences occur in the chlorine contents of the glycols prepared therefrom. This is also confirmed by the very consistent glycol melting points.

Even Substance 6, obtained by freezing it out of the hexachlorobutadiene mother liquor from Experiment 5, still yields an entirely usable glycol, even despite the fact that the starting dichloride had a melting point of only 93° to 99° C.

These results confirm that the increasing lack of homogeneity that is found in the dichlorides as the number of chlorinations performed in the same solvent increases is not localized in the aromatic nucleus, but is found partially in the side chain which contains increasingly more —$CH_2Br$-groups than —$CH_2Cl$-groups. Moreover, there is an increasing concentration of the most easily soluble o-isomers.

In conclusion it can be said that tetrabromoxylene can be subjected successfully to the chlorination several times by the reuse of the unpurified, previously used hexachlorobutadiene, without disadvantageous consequences for the further processing of the dichloride.

(c) Iron content

If a tetrabromoxylene recrystallized twice from a large amount of ethanol and having iron contents of 1 ppm or less is used, the same results are obtained if no complex former is used in the side chain chlorination. Unrecrystallized tetrabromoxylene yielded a glycol having a chlorine content of 7.5%.

EXAMPLE 3

(a) Preparation of tetrabromo-m-xylylenedichloride

As in Examples 1 and 2, 1.898 kg (4.5 moles) of artetrabromo-m-xylene (M.P. 249°–251° C., iron content 150 ppm) were chlorinated in 3 liters of hexachlorobutadiene in the presence of 1.9 g of ethylenediaminetetraacetic acid at 180° to 185° C. until bromine vapors were clearly visible, which took about 5½ hours.

The tetrabromo-m-xylene dichloride that formed crystallized upon moderate cooling of the reaction, into very slightly colored needles. These were suction filtered, washed with petroleum ether, and dried. The yield was 1.54 kg (69.8% of the theory), M.P. 171°–179° C. Upon recrystallization from methoxyethyl chloride (1:6), the product was in the form of colorless needles with a melting point of 186° to 189° C.

Elemental analysis (calculated for pure dichloride): $C_8H_4Br_4Cl_2$ (490.67)

Calculated: C 19.58%, H 0.82%, Br 65.15%, Cl 14.45%. Found: C 19.25%, H 0.80%, Br 67.1%, Cl 12.9%.

To determine the amount of bromine replaced with chlorine in the aromatic nucleus, the dichloride was transformed to the corresponding ar-tetrahalogen-m-xylylene-glycol by reaction with 2.2 moles of sodium acetate and transesterification with methanol in the presence of sodium methylate, in accordance with the procedure described in copending German Patent Application P 25 34 209.0, filed July 31, 1975, U.S. Ser. No. 709,058, filed July 27, 1976 and now U.S. Pat. No. 4,134,925 issued Jan. 16, 1979.

The raw glycol obtained was virtually colorless and had a melting point of 249°–252° C., yield 84%. 100 grams recrystallized from 750 ml of methylglycol yielded colorless needles of a melting point of 250.5°–253° C. Elemental analysis: $C_8H_6Br_{3.5}Cl_{0.5}O_2$ (431.57)

Calculated: C 22.26%, H 1.41%, Br 64.80%, Cl 4.4%, O 7.41% Found: C 22.47%, H 1.34%, Br 64.60%, Cl 4.23%, O 7.26%.

(b) Preparation of ar-tetrabromo-p-xylylenedichloride

The preparation was performed as described in Example 3(a) setting out from a tetrabromo-p-xylene containing 19 ppm of iron. Yield without processing the mother liquor: 86% Product: colorless needles, M.P. 237°–243° C. Upon recrystallization from benzene (1 g from 10 ml): M.P. 241°–244° C.

The corresponding glycol was obtained in an 88% yield, with a melting point of 248°–251° C. and a chlorine content in the nucleus of 2.2%.

(c) Preparation of ar-tetrabromo-o-xylylenedichloride

The chlorination of tetrabromo-o-xylene (17 ppm Fe) was performed similarly to the chlorinations described above, and yielded the bis-(chloromethyl) compound in a 68% yield without processing of the mother liquor, in stout crystals melting at 121°–126° C. After recrystallization (1 g from 4 ml of cyclohexane) the melting point was 126°–129° C.

The corresponding ar-tetrahalogen-o-xylyleneglycol melted at 251°–253° C. and had the composition $C_8H_6Br_{3.3}Cl_{0.7}O_2$.

(d) Preparation of ar-tetrahalogen-m-xylylenedichloride 1.84 liters (15 moles) of m-xylene were halogenated in the nucleus in 6 liters of dichloroethane in the presence of 97.3 grams (0.6 moles) of sublimated iron (III) chloride, with 1.69 liters of bromine into which 2.34 kg of chlorine had been absorbed at less than 0° C. (corresponding to 33 moles of bromine chloride). This was done by adding three quarters of the bromine chloride drop by drop at 40°–50° C., and the last quarter at 90°–100° C., to the m-xylene-dichloro-ethane-$FeCl_3$ mixture. The reaction was then allowed to continue for 3 hours at the reflux temperature of the mixture. After the mixture had been cooled to room temperature, the crystallized tetrahalogen-m-xylene was suction filtered, re-suspended in 5 liters of dichloroethane, again suction filtered, and dried. Yield: 5.815 kg (93.9%), M.P. 238°–241° C.

For further purification, the entire quantity was boiled, with stirring, in a mixture of 10 liters of water, 1.2 liters of concentrated hydrochloric acid and 1.2 liters of methanol. After suction filtration and drying: 5.711 kg, with an iron content of 60 ppm.

By elemental analysis we found the composition:

$C_8H_6Br_{3.7}Cl_{0.3}$

The ar-tetrahalogen-m-xylene thus obtained was subjected as in Examples 3a–c to side-chain chlorination, and produced in a 68% yield a dichloride melting at 166°–173° C. and having the composition $C_8H_4Br_{3.3}Cl_{0.7}$.

Setting out from o-xylene and p-xylene and following the same procedure, we obtained analogous results.

EXAMPLE 4

Side-chain chlorination of ar-octabromo-p,p'-ditolylether

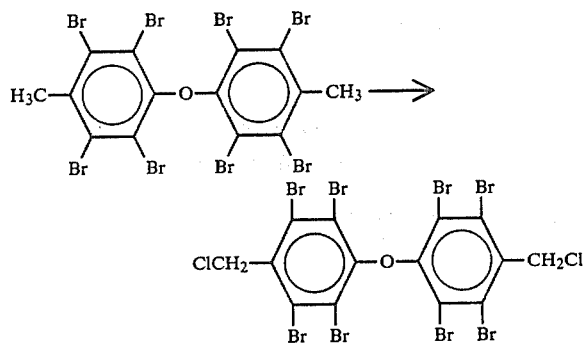

In a two-liter round flask equipped with condenser, stirrer, thermometer and gas introduction tube, 630 ml of hexachlorobutadiene, 415 g (0.5 mole) of octabromo-p,p'-ditolylether (M.P. 258°–261° C., iron content 40 ppm) and 0.45 g of ethylenediaminetetraacetic acid, were heated with stirring at 175° C.; most of the starting substance dissolved, and then the introduction of chlorine onto the surface of the slowly stirred mixture was begun. The chlorination of the side chains started immediately with a lively formation of hydrogen chloride. The introduction of chlorine was continued at a temperature around 180° C. until bromine vapors clearly appeared in the flask, which occurred after about 2½ hours, whereupon the feeding of chlorine was terminated.

A portion of the 4,4'-bis-(chloromethyl)-ar-octabromodiphenylether precipitated in the course of the chlorination. The mixture was cooled to room temperature, the brownish crystallizate was suction filtered and washed with petroleum ether, and dried. 408 g was obtained (91%) of dichloromethyl compound melting at 270°–284° C. Recrystallization from xylene (10 g from 80 ml) yielded a colorless crystallizate melting at 283°–288° C.

Elemental analysis: $C_{14}H_4Br_8Cl_2O$ (898.36)

Calculated: C 18.72%, H 0.45%, Br 71.16%, Cl 7.89%, O 1.78%. Found: C 19.09%, H 0.39%, Br 71.3%, Cl 7.6%, O 1.68%.

A repetition of the process, in which 2.075 kg (2.5 moles) of octabromo-p,p'-ditolylether, 3.1 liters of hexachlorobutadiene and 2.1 g of ethylene diamine tetraacetic acid were used, resulted in the production, after about 4 hours of chlorination at 185° C., of a 92% yield of a dichloromethyl compound melting at 281°–284° C. without recrystallization.

To determine the bromine-chlorine exchange in the nucleus, the analogous glycol was produced as described in Example 3, and after recrystallization from hexachlorobutadiene (10 g from 100 ml) it yielded colorless crystals melting at 291°–298° C.

Elemental Analysis: $C_{14}H_6Br_8O_3$ (861.47)

Calculated: C 19.52%, H 0.70%, Br 74.20%, Cl 0.00%, O 5.58%. Found: C 20.31%, H 0.71%, Br 70.61%, Cl 3.00%, O 5.49%.

This corresponds to the following crude composition:

$C_{14}H_6Br_{7.3}Cl_{0.7}O_3$ (830.34)

EXAMPLE 5

Side-chain chlorination of an ar-octahalogen-p,p'-ditolyether

In this experiment, a starting material prepared by the bromochlorination of p,p'-ditolyl ether was chlorinated on the side chains. This starting compound was obtained as follows:

(a) Bromochlorination of p,p'-ditolyl ether

In five tests, a total of 773 g (3.9 moles) of ditolyl ether was reacted with 3.962 kg (34.3 moles) of bromine chloride, using in each test the mother liquor from the preceding test. The yield was 2.968 kg with a melting point of 258°–262° C. and the composition $C_{14}H_6Br_{7.5}Cl_{0.5}$ (807)

Calculated: C 20.8%, H 0.8%, Br 74.2%, Cl 2.2%, O 2.0%. Found: C 21.3%, H 1.0%, Br 74.0%, Cl 2.2%, O 1.8%.

This corresponds to a utilization of 94% of the p,p' ditolyl ether and 80% of the bromine (without further processing of the 231 g of product in the mother liquor from the last test of the series).

A typical test is described herewith: In a four-necked flask provided with stirrer, reflux condenser, coolable dropping funnel and thermometer, 198 g (1 mole) of p,p'-ditolyl ether was dissolved in 900 ml of 1,2-dichloroethane and 16.2 g (0.1 mole) of anhydrous iron (II) chloride was added. With external cooling at 15° C., 1.016 kg (8.8 moles) of bromine chloride was added drop by drop, having previously been prepared in the dropping funnel by the introduction of chlorine into bromine, with cooling. The addition of the bromine chloride was completed in 3 hours. Then the mixture was heated slowly to the boiling temperature and refluxed for an additional 2 to 3 hours. After cooling, the product was suction filtered and stirred up in 250 ml of 1,2-dichloroethane and again suction filtered. The mother liquor was combined with the washing dichloroethane, concentrated by evaporation to 900 ml, and, after the addition of 12.2 g (0.075 mole) of anhydrous iron (III) chloride, used for the next test.

(b) Side-chain chlorination

In the apparatus described in Example 1, 2.45 kg (approx. 3 moles) of bromochlorination product prepared as in Example 5a and having the same composition as described in Example 5a and an iron content of 109 ppm, was suspended in 3.1 liters of hexachlorobutadiene, 2.5 g of ethylenediaminetetracetic acid was added and the chlorination was performed under the same conditions as in Example 1. The chlorination time was 6½ hours.

The bis-(chloromethyl) derivative that formed precipitated while the chlorination was in progress. After the mixture had cooled to room temperature, the product was suction filtered, washed with hexachlorobutadiene, then washed again with petroleum ether, and dried.

2.41 kg (92%) of a pale brownish crystallizate melting at 274°–284° C. was obtained, which upon recrystallization from xylene (10 g from 70 ml) became colorless crystals which melted at 278°–285° C. They had the composition:

$C_{14}H_4Br_{7.6}Cl_{2.4}O$ (880.58)

Calculated: C 19.09%, H 0.45%, Br 68.97%, Cl 9.66%, O 1.82%. Found: C 19.31%, H 0.41%, Br 68.70%, Cl 9.54%, O 2.01%.

The glycol prepared analogously to Example 3 (91.5% yield) melted at 291°–298° C. and had the composition:

$C_{14}H_6Br_{7.1}Cl_{0.9}O_3$ (821.49)

Calculated: C 20.47%, H 0.74%, Br 69.06%, Cl 3.88%, O 5.84%. Found: C 20.41%, H 0.66%, Br 69.32%, Cl 4.01%, O 5.66%.

EXAMPLE 6

Preparation of 4,4′-bis-(chloromethyl)-ar-octachlorodiphenylether p,p′-Ditolylether (3 moles) was chlorinated in the nucleus in hexachlorobutadiene (2 liters) in the presence of anhydrous iron (III) chloride (30 g) at 150° to 160° C. to form ar-octachloro-p,p′-ditolylether. Yield 84%.

The ar-octachloro-p,p′-ditolylether was then chlorinated on the side chains as in the preceding examples, but without complexing agents, 1.75 moles being used in 1.1 liters of hexachlorobutadiene. Chlorination time: 6½ hours at 170° C.

The yield of the bis-(chloromethyl) compound was 819 grams (87%) melting at 211°–216° C.

15 grams were recrystallized twice from 45 ml of hexachlorobutadiene each time, and then gave colorless crystals melting at 224°–227° C. and having a saponification number of 201 mg KOH per gram of substance (calculated 207).

Elemental Analysis: $C_{14}H_4Cl_{10}O$ (542.71)

Calculated: C 30.98%, H 0.75%, Cl 65.32%, O 2.95%. Found: C 30.74%, H 0.69%, Cl 65.45%, O 3.04%.

What is claimed:

1. Process for the side chains chlorination of an aromatic compound perhalogenated in the nucleus or nuclei, containing methyl groups, and having the general formula:

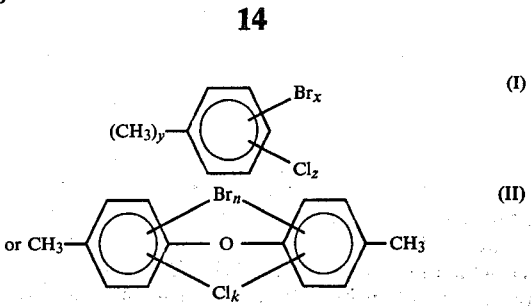

to chlorinate the methyl group(s) to —CH$_2$Cl, wherein y=1 or 2, z=0 to 1, x=6−(y+z), n=0 to 8 and k=(8−n), and the methyl groups are, respectively, in the ortho, meta or para position to one another and in the p-position to the oxygen bridge, said compound containing traces of a metal of the group Fe, Fe ion, Al, or Al ion as impurity, consisting essentially of thermally chlorinating said aromatic compound in the liquid phase, in the presence of a complexing agent for said metal, the complexing agent being of the group cyclohexylene-(1,2)-dinitrilotetraacetic acid, bis-(aminoethyl)-glycolether-N,N,N′,N′-tetraacetic acid, (3-aza-3-(carboxymethyl))-pentamethylenedinitrilotetraacetic acid; and ethylenediamine-tetraacetic acid.

2. Process of claim 1, wherein hexachlorobutadiene is used as an inert reaction medium.

3. Process of claim 1 wherein ethylenediaminetetraacetic acid is used as complexing agent for the masking of metals in an amount of 0.01 to 1 wt.-% with respect to said compound to be chlorinated.

4. Process of claim 3 wherein the complexing agent is used in amount of about 0.1% with respect to said compound to be chlorinated.

5. Process of claim 1, wherein the chlorination is performed in a temperature range of 150° to 230° C.

6. Process of claim 1, wherein the chlorination is performed in a temperature range of 170° to 200° C.

7. Process of claim 1, wherein compound II is octa-(bromo, chloro) ditolylether, and the chlorination is performed with gradual addition of chlorine, and the introduction of chlorine is terminated as soon as bromine vapor becomes apparent.

8. Process of claim 1, wherein said compound is at least one of ar-pentabromotoluene, o-, m-, and p-artetrabromoxylene, and p,p′-dimethyl-ar-octabromodiphenylether.

9. Process of claim 1, wherein said compound is of formula (I).

10. Process of claim 9, wherein said compound is perbrominated in the nucleus.

11. Process of claim 1, wherein said compound is of formula (II).

12. Process of claim 11, wherein said compound is perbrominated in the nuclei.

13. Process of claim 1, wherein (II) is octa-(bromo, chloro) ditolyether.

14. Process of claim 5, wherein (II) is octa-(bromo, chloro) ditolyether.

15. Process of claim 6, wherein (II) is octa-(bromo, chloro) ditolyether.

16. Process of claim 9, wherein the chlorination is performed at normal pressure, with gradual addition of chlorine so that chlorine reacts substantially at the rate at which it is introduced, and the introduction of chlorine is terminated is soon as bromine vapor becomes apparent.

17. Process of claim 1, wherein the chlorination is carried out by chlorination in substance, or by chlorination in the presence of inert liquid diluent.

18. Process of claim 13, wherein the chlorination is performed in the presence of hexachlorobutadiene as an inert reaction medium, and ethylenediaminetetraacetic acid as the complexing agent, at 150°–230° C., and with gradual addition of chlorine so that chlorine reacts substantially at the rate at which it is introduced, and the introduction of chlorine is terminated as soon as bromine vapor becomes apparent, whereby overchlorination of the side chain(s) is prevented.

19. Process of claim 7, wherein the chlorination is performed at normal pressure and the gradual addition of chlorine is such that the chlorine reacts substantially at the rate at which it is introduced.

20. Process of claim 1, wherein in the side chain chlorination of (II) at least some of (II) has bromine on the nucleus.

21. Process of claim 1, wherein the temperature of the thermal chlorination is 150°–230° C., and the complexing agent is active at the temperature of the thermal chlorination.

* * * * *

UNITED STATES PATENT AND TRADEMARK OFFICE
CERTIFICATE OF CORRECTION

PATENT NO. : 4,212,996
DATED : July 15, 1980
INVENTOR(S) : Egon Norbert Petersen et al.

It is certified that error appears in the above—identified patent and that said Letters Patent is hereby corrected as shown below:

| Patent | Specification | |
|---|---|---|
| Col. 13, line 65 | Claim 1, line 1 | "chains" should be "chain". |

Signed and Sealed this

Fourteenth Day of April 1981

[SEAL]

Attest:

RENE D. TEGTMEYER

Attesting Officer     Acting Commissioner of Patents and Trademarks